United States Patent
Hofmeister et al.

(10) Patent No.: US 6,958,357 B2
(45) Date of Patent: Oct. 25, 2005

(54) SUBSTITUTED BENZIMIDAZOLES, PROCESSES FOR THEIR PREPARATION, THEIR USE AS MEDICAMENTS, AND MEDICAMENTS COMPRISING THEM

(75) Inventors: Armin Hofmeister, Nierstein (DE); Uwe Heinelt, Wiesbaden (DE); Hans-Jochen Lang, Hofheim (DE); Markus Bleich, Hünfelden-Dauborn (DE); Klaus Wirth, Kriftel (DE); Michael Gekle, Würzburg (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 0 days.

(21) Appl. No.: 10/441,124

(22) Filed: May 20, 2003

(65) Prior Publication Data

US 2003/0191170 A1 Oct. 9, 2003

Related U.S. Application Data

(62) Division of application No. 10/000,028, filed on Dec. 4, 2001, now Pat. No. 6,686,384.

(30) Foreign Application Priority Data

Dec. 5, 2000 (DE) .......................... 100 60 292

(51) Int. Cl.⁷ .................. A61K 31/4184; C07D 235/04
(52) U.S. Cl. .................................. 514/398; 548/307.4
(58) Field of Search ................. 548/307.4; 514/398

(56) References Cited

U.S. PATENT DOCUMENTS

| 5,965,744 A | 10/1999 | Weichert et al. |
| 6,166,219 A | 12/2000 | Yamasaki et al. |
| 6,352,985 B1 | 3/2002 | Yamasaki et al. |

FOREIGN PATENT DOCUMENTS

| CA | 2241531 | 7/1997 |
| EP | 0640588 A1 | 3/1995 |
| GB | 1171904 | 11/1969 |
| WO | 97/24113 | 7/1997 |
| WO | WO 97/24334 A1 | 7/1997 |
| WO | 98/08818 | 3/1998 |

OTHER PUBLICATIONS

A.–M M. E. Omar, "The Cyclodesulfurization of Thio Compounds; VII. A New Facile Synthesis of $N^\alpha$–Substituted Benzimidazoles," pp 41–42 (1974).

T. Jen et al., "Amidines and Related Compounds. 6. Studies on Structure–Activity Relationships of Antihypertensive and Antisecretory Agents Related to Clonidine," *Journal of Medicinal Chemistry*, vol. 18, No. 1:90–99 (1975).

Database Caplus, Chemical Abstracts Service, "Dependence of acute toxicity on structure in a series of 2–substituted benzimidazoles," *Med. Parazitol. Parazit. Bolezni* 44(3):316–322 (1975).

Meral Tunçbilek et al., "Synthesis and Antimicrobial Activity of Some New Anilino Benzimidazoles," *Arch. Pharm. Pharm. Med. Chem.*, 330:372–376 (1997).

Abstract of HU 9900625 (search for abstract at http://pipacsweb.hpo.hu/piaopt/pia04_09.htm?v=hunpia&a=start).

*Primary Examiner*—Golam M. M. Shameem
(74) *Attorney, Agent, or Firm*—Finnegan, Henderson, Farabow, Garrett & Dunner, L.L.P.

(57) ABSTRACT

The invention relates to the use of compounds of formula I for the production of a medicament for the treatment of illnesses which can be influenced by inhibition of the Na+/H+ exchanger, and to a medicament comprising them.

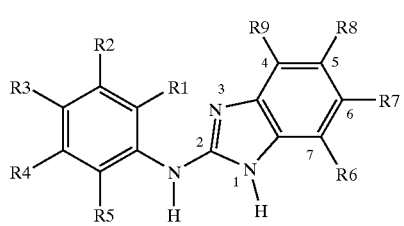

in which R1 to R9 have the meanings shown in the claims.

18 Claims, No Drawings

SUBSTITUTED BENZIMIDAZOLES, PROCESSES FOR THEIR PREPARATION, THEIR USE AS MEDICAMENTS, AND MEDICAMENTS COMPRISING THEM

This is a division of application Ser. No. 10/000,028, filed Dec. 4, 2001, now U.S. Pat. No. 6,686,384 which is incorporated herein by reference.

This application claims the benefit of the filing date of German Patent Application Number 10060292.4, filed on Dec. 5, 2000, which application is hereby incorporated by reference.

The invention relates to substituted benzimidazoles of formula I

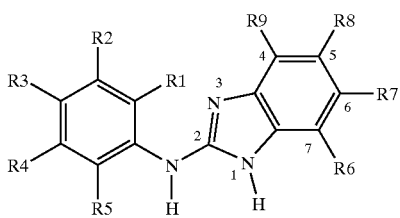

in which:
R1 and R5 are, independently of one another, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are, independently of one another, OH or O-alkyl having 1 to 4 carbon atoms, in which alkyl is unsubstituted or partially or completely substituted by fluorine; or R1 and R5 are, independently of one another, OCOR10, NR11R12, COR13, COOH, COOR14, CONR11R12, or —(O)$_n$—SO$_m$R15, in which n is 0 or 1 and m is 0, 1, or 2; or R1 and R5 are O-phenyl, in which phenyl is unsubstituted or substituted by one to three substituents selected, independently of one another, from F, Cl, Br, I, alkyl having 1 to 4 carbon atoms, OH, O-alkyl having 1 to 4 carbon atoms, NR16R17, CN, or ($C_1$–$C_4$)-alkylsulfonyl, in which the alkyl groups are unsubstituted or partially or completely substituted by fluorine;

R16 and R17 are, independently of one another, H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one CH$_2$ group of said alkyl is optionally replaced by O or NR18; or R11 and R12, together with the nitrogen atom to which they are bonded, form a 5-, 6-, or 7-membered ring; or R11 and R12 are, independently of one another, COR19 or SO$_2$R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one CH$_2$ group of said alkyl is optionally replaced by O or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

but R1 and R5 cannot simultaneously be Cl or CH$_3$;

R2, R3, and R4 are H or one of the radicals R2, R3, or R4 is optionally F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are, independently of one another, OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one CH$_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt or trifluoroacetate thereof.

Other embodiments of compounds of formula I are those in which:

R1 and R5 are, independently of one another, F, Cl, Br, CN, alkyl having 1 to 4 carbon atoms, CF$_3$, CH$_2$CF$_3$, CF$_2$CF$_3$, cycloalkyl having 3 to 7 carbon atoms, O-alkyl having 1 to 4 carbon atoms, OH, OCF$_3$, OCH$_2$CF$_3$, OCF$_2$CF$_3$, OCOR10, NR11R12, COR13, COOH, COOR14, CONR11R12, —O$_m$—SO$_2$R15, or O-phenyl;

m is 0 or 1;

R10 is H, alkyl having 1 to 4 carbon atoms, CF$_3$, CH$_2$CF$_3$, or CF$_2$CF$_3$;

R11 and R12 are, independently of one another, H, alkyl having 1 to 4 carbon atoms, CF$_3$, CH$_2$CF$_3$, CF$_2$CF$_3$, and at least one CH$_2$ group of said alkyl is optionally replaced by O or NR18; or R11 and R12, together with the nitrogen atom to which they are bonded, form a 5-, 6-, or 7-membered ring; or R11 and R12 are, independently of one another, COR19 or SO$_2$R20;

R18, R19, and R20 are, independently of one another, H, alkyl having 1 to 4 carbon atoms, $CF_3$, $CH_2CF_3$, or $CF_2CF_3$;

R13 and R14 are, independently of one another, alkyl having 1 to 4 carbon atoms, $CF_3$, $CH_2CF_3$, or $CF_2CF_3$;

R15 is alkyl having 1 to 4 carbon atoms, $CF_3$, $CH_2CF_3$, $CF_2CF_3$, OH, O-alkyl having 1 to 4 carbon atoms, $OCF_3$, $OCH_2CF_3$, $OCF_2CF_3$, or NR21R22;

R21 and R22 are, independently of one another, H, alkyl having 1 to 4 carbon atoms, $CF_3$, $CH_2CF_3$, or $CF_2CF_3$; or R21 and R22, together with the nitrogen atom to which they are bonded, are $-(CH_2)_4-$, $-(CH_2)_5-$, $-(CH_2)_2-O-(CH_2)_2-$, or $-(CH_2)_2-N-R30-(CH_2)_2$;

R30 is H, $CH_3$, or $CF_3$;

but R1 and R5 cannot simultaneously be Cl or $CH_3$;

R2, R3, and R4 are H or one of the radicals R2, R3, or R4 is optionally F;

R6, R7, R8, and R9 are, independently of one another, H, F, Cl, Br, I, CN, alkyl having 1 to 4 carbon atoms, $CF_3$, $CH_2CF_3$, $CF_2CF_3$, cycloalkyl having 3 to 7 carbon atoms, OH, O-alkyl having 1 to 4 carbon atoms, $OCF_3$, $OCH_2CF_3$, $OCF_2CF_3$, OCOR24, or NR25R26;

R24 is H, alkyl having 1 to 4 carbon atoms, $CF_3$, $CH_2CF_3$, or $CF_2CF_3$;

R25 and R26 are, independently of one another, H, alkyl having 1 to 4 carbon atoms, $CF_3$, $CH_2CF_3$, $CF_2CF_3$, or COR27; or R25 and R26, together with the nitrogen atom to which they are bonded, form a 5-, 6-, or 7-membered ring;

R27 is H, alkyl having 1 to 4 carbon atoms, $CF_3$, $CH_2CF_3$, or $CF_2CF_3$; or a pharmaceutically tolerable salt or trifluoroacetate thereof.

Another embodiment of compounds of formula I are those in which:

R1 and R5 are, independently of one another, F, Cl, Br, CN, methyl, ethyl, isopropyl, $CF_3$, cyclopropyl, OH, O-methyl, O-ethyl, O-isopropyl, $OCF_3$, O-acetyl, $NH_2$, $N(CH_3)_2$, $N(CH_2CH_3)_2$, N-pyrrolidino, N-piperidino, N-morpholino, N-(N'-methyl)-piperazino, $NHSO_2Me$, acetyl, COOH, COOR14, CONR11R12, $SO_2R15$, or O-phenyl;

R11 and R12 are, independently of one another, H, methyl, or ethyl;

R14 is methyl or ethyl;

R15 is $CH_3$, $CF_3$, OH, $OCH_3$, $OCF_3$, or NR21R22;

R21 and R22 are, independently of one another, H or methyl;

but R1 and R5 cannot simultaneously be Cl or $CH_3$;

R2, R3, and R4 are H;

R6, R7, R8, and R9 are, independently of one another, H, F, Cl, CN, $CH_3$, $C_2H_5$, isopropyl, $CF_3$, cyclopropyl, OH, $OCH_3$, $OCF_3$, O-acetyl, or NR25R26;

R25 and R26 are, independently of one another, H, methyl, or acetyl; or a pharmaceutically tolerable salt or trifluoroacetate thereof.

Another embodiment of compounds of formula I are those in which:

R1 and R5 are, independently of one another, F, Cl, Br, CN, methyl, ethyl, isopropyl, $CF_3$, cyclopropyl, OH, O-methyl, O-ethyl, O-isopropyl, $OCF_3$, O-acetyl, $NH_2$, $N(CH_3)_2$, $N(CH_2CH_3)_2$, N-pyrrolidino, N-piperidino, N-morpholino, N-(N'-methyl)-piperazino, $NHSO_2Me$, acetyl, COOH, COOR14, CONR11R12, $SO_2R15$, or O-phenyl;

R11 and R12 are, independently of one another, H, methyl, or ethyl;

R14 is methyl or ethyl;

R15 is $CH_3$, $CF_3$, OH, $OCH_3$, $OCF_3$, or NR21R22;

R21 and R22 are, independently of one another, H or methyl;

but R1 and R5 cannot simultaneously be Cl or $CH_3$;

R2, R3, and R4 are H;

R6 and R9 are, independently of one another, H, F, Cl, CN, $CH_3$, $CF_3$, cyclopropyl, OH, $OCH_3$, $OCF_3$, O-acetyl, or NR25R26;

R25 and R26 are, independently of one another, H, methyl, or acetyl;

R7 and R8 are, independently of one another, H, F, or OH; or a pharmaceutically tolerable salt or trifluoroacetate thereof.

Examples of compounds of formula I are:

(1H-benzimidazol-2-yl)-(2,6-dichlorophenyl)amine;

2-(2,6-dichlorophenylamino)-1H-benzimidazol-4-ol;

(1H-benzimidazol-2-yl)-(2,6-dimethylphenyl)amine;

(1H-benzimidazol-2-yl)-(2-chloro-6-methylphenyl)amine;

(2,6-dichlorophenyl)-(5,6-difluoro-1H-benzimidazol-2-yl)amine;

(2,6-dichlorophenyl)-(4-methyl-1H-benzimidazol-2-yl)amine;

(1H-benzimidazol-2-yl)-(2-chloro-6-fluorophenyl)amine;

(1H-benzimidazol-2-yl)-(2,6-dibromophenyl)amine;

2-(2,6-dichlorophenylamino)-5-fluorobenzimidazole;

2-(2,6-dichlorophenylamino)-4-fluorobenzimidazole;

2-(2-trifluoromethyl-6-chlorophenylamino)benzimidazole;

2-(2,6-dichlorophenylamino)-4,5-difluorobenzimidazole;

2-(2,6-dichlorophenylamino)-5-hydroxybenzimidazole;

2-(2,6-dichlorophenylamino)-4,5,6,7-tetrafluorobenzimidazole;

2-(2,6-dichlorophenylamino)-4,6-difluorobenzimidazole;

(1H-benzimidazol-2-yl)-(2-chlorophenyl)amine;

(1H-benzimidazol-2-yl)-(2-trifluoromethylphenyl)amine;

(1H-benzimidazol-2-yl)-(2-bromophenyl)amine; and (1H-benzimidazol-2-yl)-o-tolylamine; or a pharmaceutically tolerable salt or trifluoroacetate thereof.

In addition, the invention comprises the use of substituted benzimidazoles of formula I for the production of a medicament for the treatment of diseases which are influenced by the NHE3 exchange inhibitor, in which:

R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or $-(O)_n-SO_mR15$, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or $(C_1-C_4)$- alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one $CH_2$ group of said alkyl is optionally replaced by O or NR18; or R11 and R12, together with the nitrogen atom to which they are bonded, form a 5-, 6-, or 7-membered ring; or R11 and R12 are COR19 or $SO_2$R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one $CH_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

Other embodiments comprise the use of compounds of formula I in which:

R1 and R5 are, independently of one another, H, F, Cl, Br, CN, alkyl having 1 to 4 carbon atoms, $CF_3$, $CH_2CF_3$, $CF_2CF_3$, cycloalkyl having 3 to 7 carbon atoms, O-alkyl having 1 to 4 carbon atoms, OH, $OCF_3$, $OCH_2CF_3$, $OCF_2CF_3$, OCOR10, NR11R12, COR13, COOH, COOR14, CONR11R12, —$O_m$—$SO_2$R15, or O-phenyl;

m is 0 or 1;

R10 is H, alkyl having 1 to 4 carbon atoms, $CF_3$, $CH_2CF_3$, or $CF_2CF_3$;

R11 and R12 are, independently of one another, H, alkyl having 1 to 4 carbon atoms, $CF_3$, $CH_2CF_3$, $CF_2CF_3$, and at least one $CH_2$ group of said alkyl is optionally replaced by O or NR18; or R11 and R12, together with the nitrogen atom to which they are bonded, form a 5-, 6-, or 7-membered ring; or R11 and R12 are COR19 or $SO_2$R20;

R18, R19, and R20 are, independently of one another, H or alkyl having 1 to 4 carbon atoms, $CF_3$, $CH_2CF_3$, or $CF_2CF_3$;

R13 and R14 are alkyl having 1 to 4 carbon atoms, $CF_3$, $CH_2CF_3$, or $CF_2CF_3$;

R15 is alkyl having 1 to 4 carbon atoms, $CF_3$, $CH_2CF_3$, $CF_2CF_3$, OH, O-alkyl having 1 to 4 carbon atoms, $OCF_3$, $OCH_2CF_3$, $OCF_2CF_3$, or NR21R22;

R21 and R22 are, independently of one another, H, alkyl having 1 to 4 carbon atoms, $CF_3$, $CH_2CF_3$, or $CF_2CF_3$; or R21 and R22, together with the nitrogen atom to which they are bonded, are —$(CH_2)_4$—, —$(CH_2)_5$—, —$(CH_2)_2$—O—$(CH_2)_2$—, or —$(CH_2)_2$—N—R30-$(CH_2)_2$;

R30 is H, $CH_3$, or $CF_3$;

but R1 and R5 cannot simultaneously be Cl or $CH_3$, and at most one of the substituents R1 and R5 is hydrogen;

R2, R3, and R4 are, independently of one another, H or F;

R6, R7, R8, and R9 are, independently of one another, H, F, Cl, Br, I, CN, alkyl having 1 to 4 carbon atoms, $CF_3$, $CH_2CF_3$, $CF_2CF_3$, cycloalkyl having 3 to 7 carbon atoms, OH, O-alkyl having 1 to 4 carbon atoms, $OCF_3$, $OCH_2CF_3$, $OCF_2CF_3$, OCOR24, or NR25R26;

R24 is H, alkyl having 1 to 4 carbon atoms, $CF_3$, $CH_2CF_3$, or $CF_2CF_3$;

R25 and R26 are, independently of one another, H, alkyl having 1 to 4 carbon atoms, $CF_3$, $CH_2CF_3$, $CF_2CF_3$, or COR27; or R25 and R26, together with the nitrogen atom to which they are bonded, form a 5-, 6-, or 7-membered ring;

R27 is H, alkyl having 1 to 4 carbon atoms, $CF_3$, $CH_2CF_3$, or $CF_2CF_3$; or a pharmaceutically tolerable salt thereof.

Other embodiments comprise the use of compounds of formula I in which:

R1 and R5 are, independently of one another, H, F, Cl, Br, CN, methyl, ethyl, isopropyl, $CF_3$, cyclopropyl, OH, O-methyl, O-ethyl, O-isopropyl, $OCF_3$, O-acetyl, $NH_2$, $N(CH_3)_2$, $N(CH_2CH_3)_2$, N-pyrrolidino, N-piperidino, N-morpholino, N-(N'-methyl)-piperazino, $NHSO_2Me$, acetyl, COOH, COOR14, CONR11R12, $SO_2$R15, or O-phenyl;

R11 and R12 are, independently of one another, H, methyl, or ethyl;

R14 is methyl or ethyl;

R15 is $CH_3$, $CF_3$, OH, $OCH_3$, $OCF_3$, or NR21R22;

R21 and R22 are, independently of one another, H or methyl;

but R1 and R5 cannot simultaneously be Cl or $CH_3$, and at most one of the substituents R1 and R5 is hydrogen;

R2, R3, and R4 are H;

R6, R7, R8, and R9 are, independently of one another, H, F, Cl, CN, CH$_3$, C$_2$H$_5$, isopropyl, CF$_3$, cyclopropyl, OH, OCH$_3$, OCF$_3$, O-acetyl, or NR25R26;

R25 and R26 are, independently of one another, H, methyl, or acetyl; or a pharmaceutically tolerable salt thereof.

Another embodiment comprises the use of compounds of formula I in which:

R1 and R5 are, independently of one another, F, Cl, Br, CN, methyl, ethyl, isopropyl, CF$_3$, cyclopropyl, OH, O-methyl, O-ethyl, O-isopropyl, OCF$_3$, O-acetyl, NH$_2$, N(CH$_3$)$_2$, N(CH$_2$CH$_3$)$_2$, N-pyrrolidino, N-piperidino, N-morpholino, N-(N'-methyl)-piperazino, NHSO$_2$Me, acetyl, COOH, COOR14, CONR11R12, SO$_2$R15, or O-phenyl;

R11 and R12 are, independently of one another, H, methyl, or ethyl;

R14 is methyl or ethyl;

R15 is CH$_3$, CF$_3$, OH, OCH$_3$, OCF$_3$, or NR21R22;

R21 and R22 are, independently of one another, H or methyl;

but R1 and R5 cannot simultaneously be Cl or CH$_3$, and at most one of the substituents R1 and R5 is hydrogen;

R2, R3, and R4 are H;

R6 and R9 are, independently of one another, H, F, Cl, CN, CH$_3$, CF$_3$, cyclopropyl, OH, OCH$_3$, OCF$_3$, O-acetyl, or NR25R26;

R25 and R26 are, independently of one another, H, methyl, or acetyl;

R7 and R8 are, independently of one another, H, F, or OH; or a pharmaceutically tolerable salt thereof.

Examples comprising the use of compounds of formula I are:

1: (1H-benzimidazol-2-yl)-(2,6-dichlorophenyl)amine;
2: 2-(2,6-dichlorophenylamino)-1H-benzimidazol-4-ol;
3: (1H-benzimidazol-2-yl)-(2,6-dimethylphenyl)amine;
4: (1H-benzimidazol-2-yl)-(2-chloro-6-methylphenyl)amine;
5: (2,6-dichlorophenyl)-(5,6-difluoro-1H-benzimidazol-2-yl)amine;
6: (2,6-dichlorophenyl)-(4-methyl-1H-benzimidazol-2-yl)amine;
7: (1H-benzimidazol-2-yl)-(2-chloro-6-fluorophenyl)amine;
8: (1H-benzimidazol-2-yl)-(2,6-dibromophenyl)amine;
9: 2-(2,6-dichlorophenylamino)-5-fluorobenzimidazole;
10: 2-(2,6-dichlorophenylamino)-4-fluorobenzimidazole;
11: 2-(2-trifluoromethyl-6-chlorophenylamino)benzimidazole;
12: 2-(2,6-dichlorophenylamino)-4,5-difluorobenzimidazole;
13: 2-(2,6-dichlorophenylamino)-5 hydroxybenzimidazole;
14: 2-(2,6-dichlorophenylamino)-4,5,6,7-tetrafluorobenzimidazole;
15: 2-(2,6-dichlorophenylamino)-4,6-difluorobenzimidazole;
16: (1H-benzimidazol-2-yl)-(2-chlorophenyl)amine;
17: (1H-benzimidazol-2-yl)-(2-trifluoromethylphenyl)amine;
18: (1H-benzimidazol-2-yl)-(2-bromophenyl)amine; and
19: (1H-benzimidazol-2-yl)-o-tolylamine; or a pharmaceutically tolerable salt thereof.

If compounds of formula I contain one or more centers of asymmetry, these can have either the S or the R configuration. The compounds can be present as optical isomers, as diastereomers, as racemates, or as mixtures thereof.

Compounds of formula I can furthermore be present as tautomers or as a mixture of tautomeric structures. In the case of substitution on the corresponding N atoms of the benzimidazole structure, the compounds can be present in the form of the various double bond isomers or as a mixture of the double bond isomers.

The designated alkyl radicals or partially or completely fluorinated alkyl radicals can be either straight-chain or branched.

CH$_2$ units are also the terminal CH$_3$ groups in an alkyl chain, which are interpreted in this connection as CH$_2$—H groups.

The expression "5-, 6-, or 7-membered ring" represents a 5-membered to 7-membered heterocyclic ring comprising at least one alkyl or heteroatom. Examples of heteroatoms are nitrogen, oxygen, and sulfur. If multiple heteroatoms are contained, these can be identical or different.

Methods for the preparation of the compounds used are also described. Thus, compounds of formula I can be prepared in the manner known to the person skilled in the art from the underlying isothiocyanates of formula II and the corresponding phenylenediamines of formula III.

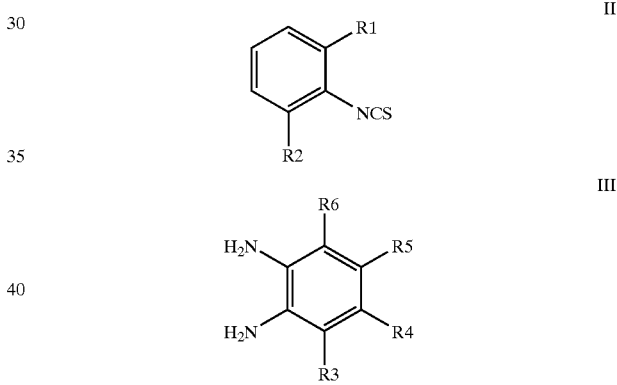

The thiourea intermediately formed here is cyclized to the corresponding compounds of formula I by means of mercury (II) oxide (J. Med. Chem., 18, 90–99 (1975)), methyl iodide (Synthesis, 41–42 (1974)), or carbodiimide (Synthesis, 864–865 (1977)). The isothiocyanates of formula II used here, if not commercially obtainable, can be prepared in the manner known from the literature from the corresponding anilines by the methods known to the person skilled in the art, e.g., by treating with thiophosgene (J. Med. Chem., 18, 90–99 (1975)) orthiocarbonyldiimidazole (Justus Liebigs Ann. Chem., 657 (1962)).

Likewise, starting from the anilines, by treating with NaOH, carbon disulphide, and methyl iodide in processes which are already known from the literature, it is possible to prepare the corresponding N-aryldithiocarbamates (Synthesis, 961 (1981)) and, from these in turn, the N-aryldithiocarboximidates of formula IV (Synthesis, 375 (1983)), which can be reacted in the presence of the phenylenediamines of formula III at elevated temperatures to give the desired compounds of formula I.

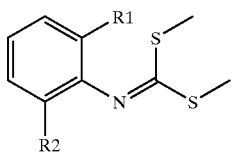

Finally, compounds of formula I can be prepared starting from the anilines and the corresponding 2-substituted benzimidazoles of formula V by heating.

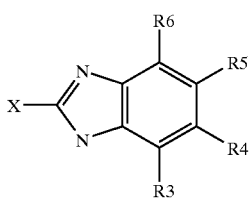

X in this case is a leaving group, such as, for example, Cl, Br, or SO₃H (J. Org. Chem., 51, 1882 (1986)).

British patent specification 1 171 904 describes a general formula which would even allow o,o-disubstitution in the aniline moiety. However, there is no indication of compounds of formula I actually taken into consideration which have an o,o-disubstitution pattern, let alone an experimental description. The compounds described in this British patent specification 1 174 904 are protected therein as substances having antibacterial activity. In the case of compounds according to the invention, it was not possible with the aid of an exemplary compound to detect any antibacterial action, such that the substance class according to British patent specification 1 171 904 can be differentiated clearly from the compounds according to the invention, both structurally and in its pharmacological properties.

Furthermore, some of the benzimidazoles according to the invention could be constructed from WO 9808818, which are described therein as phospholipase inhibitors. However, no single representative of this class of compound is described therein, neither experimentally nor pharmacologically.

It was possible to show that compounds of formula I are outstanding inhibitors of the sodium-hydrogen exchanger (NHE)—in particular, of the sodium-hydrogen exchanger of subtype 3 (NHE3).

On account of these properties, the compounds are suitable for the treatment of diseases which are caused by oxygen deficiency. As a result of their pharmacological properties, the compounds are outstandingly suitable as antiarrhythmic medicaments having a cardioprotective component for infarct prophylaxis and infarct treatment and for the treatment of angina pectoris, which also preventively inhibit or greatly decrease the pathophysiological processes in the formation of ischemically induced damage, in particular, in the triggering of ischemically induced cardiac arrhythmias. Because of their protective actions against pathological hypoxic and ischemic situations, compounds of formula I can be used, as a result of the inhibition of the cellular Na+/H+ exchange mechanism, as medicaments for the treatment of all acute or chronic damage caused by ischemia or diseases induced primarily or secondarily thereby. This relates to their use as medicaments for surgical interventions, e.g., in organ transplants, where the compounds can be used both for the protection of the organs in the donor before and during removal, for the protection of removed organs, for example, during treatment with or storage thereof in physiological fluids, and during surgical transfer to the recipient's body. The compounds are likewise valuable, protectively acting medicaments when carrying out angioplastic surgical interventions, for example, on the heart and on peripheral vessels. Corresponding to their protective action against ischemically induced damage, the compounds are also suitable as medicaments for the treatment of ischemias of the nervous system, in particular, of the CNS, where they are suitable, for example, for the treatment of stroke or of cerebral edema. Moreover, compounds of formula I used according to the invention are likewise suitable for the treatment of forms of shock, such as, for example, of allergic, cardiogenic, hypovolemic, and of bacterial shock.

Furthermore, the compounds induce an improvement in the respiratory drive and are therefore used for the treatment of respiratory conditions in the following clinical conditions and diseases: disturbed central respiratory drive (e.g., central sleep apneas, sudden infant death, postoperative hypoxia), muscular-related respiratory disorders, respiratory disorders after long-term respiration, respiratory disorders during adaptation in a high mountainous area, obstructive and mixed forms of sleep apnea, and acute and chronic lung diseases with hypoxia and hypercapnia.

The compounds additionally increase the muscle tone of the upper airways such that snoring is suppressed.

A combination of an NHE inhibitor with a carboanhydrase inhibitor (e.g., acetazol-amide), where the latter produces a metabolic acidosis and thereby even increases the respiratory activity, proves advantageous due to increased action and decreased use of active substance.

It has been shown that compounds used according to the invention have a mild laxative action and accordingly can be used advantageously as laxatives or in the case of threatening intestinal blockage, where the prevention of ischemic damage accompanying blockages in the intestinal area is particularly advantageous.

The possibility furthermore exists of preventing gallstone formation.

Moreover, compounds of formula I used according to the invention are distinguished by strong inhibitory action on the proliferation of cells, for example, fibroblast cell proliferation and the proliferation of the vascular smooth muscle cells. Therefore, compounds of formula I are suitable as valuable therapeutics for diseases in which cell proliferation is a primary or secondary cause, and can therefore be used as antiatherosclerotic agents against diabetic late complications, cancers, fibrotic diseases such as pulmonary fibrosis, fibrosis of the liver or fibrosis of the kidneys, and organ hypertrophies and hyperplasias, in particular, in prostate hyperplasia or prostate hypertrophy.

Compounds used according to the invention are effective inhibitors of the cellular sodium-proton antiporter (Na/H exchanger), which is raised in numerous diseases (e.g., essential hypertension, atherosclerosis, diabetes), even in those cells which are accessible to measurements, such as, for example, in erythrocytes, platelets, or leukocytes. Compounds used according to the invention are therefore suitable as outstanding and simple scientific tools, for example, in their use as diagnostics for the determination and differentiation of certain forms of hypertension, but also of atherosclerosis, diabetes, and proliferative diseases. Moreover, compounds of formula I are suitable for preventive therapy for the prevention of the genesis of high blood pressure, for example, of essential hypertension.

It has additionally been found that NHE inhibitors exhibit a favorable influence on the serum lipoproteins. It is generally recognized that for the formation of arteriosclerotic vascular changes, in particular, of a heart disease, excessively high blood lipid levels, 'hyperlipoproteinemia' is a significant risk factor. For the prophylaxis and the regression of atherosclerotic changes, the lowering of raised serum lipoproteins therefore assumes extreme importance. Compounds used according to the invention can therefore be used for the prophylaxis and for the regression of atherosclerotic changes, by excluding a causal risk factor. With this protection of the vessels against the syndrome of endothelial dysfunction, compounds of formula I are valuable medicaments for the prevention and for the treatment of coronary vasospasms, atherogenesis, and atherosclerosis, left-ventricular hypertrophy and dilated cardiomyopathy, and thrombolytic diseases.

The compounds mentioned are therefore advantageously used for the production of a medicament for the prevention and treatment of sleep apneas and muscle-related respiratory disorders; for the production of a medicament for the prevention and treatment of snoring; for the production of a medicament for lowering blood pressure; for the production of a medicament for the prevention and treatment of diseases which are induced by ischemia and reperfusion of central and peripheral organs, such as, for example, acute kidney failure, stroke, endogenous states of shock, and intestinal diseases; for the production of a medicament for the treatment of diabetic late damage and chronic kidney diseases, in particular, of all kidney inflammations (nephritides) which are associated with increased protein/albumin excretion; for the production of a medicament for the treatment of attack by ectoparasites in human and veterinary medicine; for the production of a medicament for the treatment of the diseases mentioned in combination with blood pressure-lowering substances, typically with angiotensin-converting enzyme (ACE) inhibitors, with diuretics and saluretics such as furosemide, hydrochlorothiazide, pseudoaldosterone antagonists, and aldosterone antagonists, and with angiotensin receptor antagonists.

The administration of sodium-proton exchange inhibitors of formula I as novel medicaments for the lowering of raised blood lipid levels is claimed, and the combination of sodium-proton exchange inhibitors with medicaments having blood pressure-lowering and/or hypolipidemic action.

Typically, the compounds mentioned are advantageously used for the production of a medicament for the prevention and treatment of sleep apneas and muscle-related respiratory disorders; for the production of a medicament for the prevention and treatment of snoring; for the production of a medicament for lowering blood pressure; for the production of a medicament for the prevention and treatment of diseases which are induced by ischemia and reperfusion of central and peripheral organs, such as, for example, acute kidney failure and intestinal diseases; for the production of a medicament for the treatment of diabetic late damage and chronic kidney diseases, in particular, of all kidney inflammations (nephritides) which are associated with increased protein/albumin excretion; for the production of a medicament for the treatment of attack by ectoparasites in human and veterinary medicine; for the production of a medicament for the treatment of the diseases mentioned in combination with blood pressure-lowering substances, preferably with angiotensin-converting enzyme (ACE) inhibitors, with diuretics and saluretics such as furosemide, hydrochlorothiazide, pseudoaldosterone antagonists, and aldosterone antagonists, with adenosine receptor modulators, in particular, with adenosine receptor activators (A2 agonists), and with angiotensin receptor antagonists.

Pharmaceuticals which contain a compound of formula I can in this case be administered orally, parenterally, intravenously, rectally, transdermally, or by inhalation, the administration being dependent on the particular clinical picture of the disease. Compounds of formula I can in this case be administered on their own or together with pharmaceutical excipients, namely both in veterinary and in human medicine.

The person skilled in the art is familiar on the basis of his/her expert knowledge with excipients which are suitable for the desired pharmaceutical formulation. In addition to solvents, gel formers, suppository bases, tablet excipients, and other active compound carriers, it is possible to use, for example, antioxidants, dispersants, emulsifiers, antifoams, flavor corrigents, preservatives, solubilizers, or colorants.

For an oral administration form, the active compounds are mixed with the additives suitable therefor, such as vehicles, stabilizers, or inert diluents, and brought by the customary methods into the suitable administration forms, such as tablets, coated tablets, hard gelatin capsules, aqueous, alcoholic, or oily solutions. Inert excipients which can be used are, for example, gum arabic, magnesia, magnesium carbonate, potassium phosphate, lactose, glucose, or starch, in particular, cornstarch. In this case, preparation can be carried out both as dry and moist granules. Suitable oily vehicles or solvents are, for example, vegetable or animal oils, such as sunflower oil or cod liver oil.

For subcutaneous or intravenous administration, the active compounds used, if desired with the substances customary therefor, such as solubilizers, emulsifiers, or further excipients, are brought into solution, suspension, or emulsion. Possible solvents are, for example, water, physiological saline solution, or alcohols (e.g., ethanol, propanol, and glycerol). In addition, other possible solvents are sugar solutions such as glucose or mannitol solutions, or alternatively a mixture of the various solvents mentioned.

Pharmaceutical formulations which are suitable for administration in the form of aerosols or sprays are, for example, solutions, suspensions, or emulsions of the active compound of formula I in a pharmaceutically acceptable solvent, such as, ethanol or water, or a mixture of such solvents.

If required, the formulation can also contain other pharmaceutical excipients such as surfactants, emulsifiers, and stabilizers, and a propellant. Such a preparation customarily contains the active compound in a concentration of approximately 0.1 to 10%, typically, of approximately 0.3 to 3%, by weight.

As used here, treatment includes therapy for a particular disease, such as treating diseases which are influenced by inhibition of the $Na^+/H^+$ exchanger. In this respect, treatment can mean successfully eliminating the disease, reducing the effects associated with it, and/or reducing its severity. Treatment also includes prevention or prophylaxis of the onset of a disease by treating patients falling into a risk group or category for developing a particular disease or by treating patients after a successful treatment to prevent reoccurrence of the treated disease. Those skilled in the art can routinely identify patients likely to present with a disease, thereby qualifying as candidates for prevention therapy, because of factors such as diet, habits (e.g., smoking), family history for the disease, etc.

The dose of the active compound of formula I to be administered and the frequency of administration depend on the potency and duration of action of the compounds used;

moreover, also on the nature and severity of the illness to be treated and on the sex, age, weight, and individual responsiveness of the mammal to be treated.

On average, the daily dose of a compound of formula I in the case of a patient weighing approximately 75 kg is at least 0.001 mg/kg, typically 0.01 mg/kg, to at most 10 mg/kg, usually 1 mg/kg, of body weight. In the case of acute episodes of the disease, for example, immediately after suffering a cardiac infarct, even higher and especially more frequent doses may also be necessary, e.g., up to 4 individual doses per day. In particular, in the case of i.v. administration, for example, in the case of an infarct patient in the intensive care unit, up to 200 mg per day may be necessary.

EXPERIMENTAL DESCRIPTIONS AND EXAMPLES

List of Abbreviations Used:

| | |
|---|---|
| $R_t$ | Retention time |
| TFA | Trifluoroacetic acid |
| LCMS | Liquid chromatography-mass spectroscopy |
| MS | Mass spectroscopy |
| CI | Chemical Ionization |
| RT | Room temperature |
| THF | Tetrahydrofuran |
| EA | Ethyl Acetate |

General:

The retention times ($R_t$) indicated below relate to LCMS measurements having the following parameters:

| | |
|---|---|
| stationary phase: | Merck Purospher 3µ2 × 55 mm |
| mobile phase: | 95% H$_2$O (0.05% TFA)→ 95% acetonitrile; 4 min; 95% acetonitrile; 1.5 min → 5% acetonitrile; 1 min; 0.5 ml/min |

Example 1

(1H-Benzimidazol-2-yl)-(2,6-dichlorophenyl)amine hydrochloride

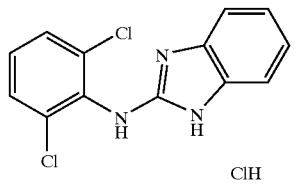

(1H-Benzimidazol-2-yl)-(2,6-dichlorophenyl)amine was prepared according to methods known from the literature (J. Med. Chem., 18, 90 (1975)). Recrystallization from hot, dilute hydrochloric acid yielded the corresponding hydrochloride as a colorless solid.

LCMS-$R_t$=3.605 min; MS-Cl: 278.2, 280.0

Example 2

2-(2,6-Dichlorophenylamino)-1H-benzimidazol-4-ol Hydrochloride

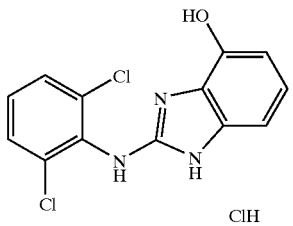

Intermediate 1: 1-(2-Amino-6 hydroxyphenyl)-3-(2,6-dichlorophenyl)thiourea 1.0 equivalent of 2,6-dichlorophenyl isothiocyanate was treated with 1.0 equivalent of 2,3-diaminophenol and heated to reflux for 1 h. After cooling to RT, the precipitate was filtered off with suction, washed with ether, and dried. The desired thiourea was obtained in a yield of 61%. M.p.: 202–204° C.

2-(2,6-Dichlorophenylamino)-1H-benzimidazol-4-ol hydrochloride

Intermediate 1 was dissolved in ethanol and treated with 8 equivalents of methyl iodide. The mixture was heated to reflux for 8 h. After it cooled to RT, the reaction solution was filtered through activated carbon and the filtrate was concentrated in vacuo. The residue was treated with 0.5 N HCl and the precipitate was filtered off with suction after 30 min. The residue was stirred once more with EA and dried. The title compound was isolated in a yield of 47%. M.p.: 333–335° C.

MS(Cl+): 294.1; 296.1

Example 3

(1H-Benzimidazol-2-yl)-(2,6-dimethylphenyl)amine trifluoracetate

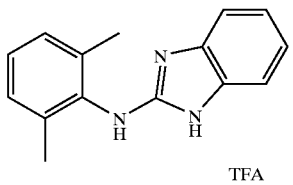

2,6-Dimethylaniline (0.5 g) and 2-chlorobenzimidazole (0.63 g) were mixed in a flask and then kept at 200° C. for 2 h. After cooling, the residue was dissolved out of the flask with 1 N HCl at boiling heat. The material dissolved out was then stirred at RT for 30 min, then the insoluble material was filtered off with suction and the filtrate was evaporated. The residue was purified by means of preparative HPLC on RP-18 using acetonitrile/water (0.05% TFA). The clean fractions were combined, concentrated, and then recrystallized from acetonitrile/water. 500 mg of white crystals were obtained.

LCMS-$R_t$: 3.30 min; MS (ES+, M+H$^+$): 238.1

Example 4

(1H-Benzimidazol-2-yl)-(2-chloro-6-methylphenyl)amine hydrochloride

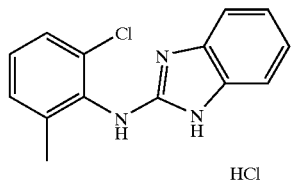

HCl

2-Chloro-6-methylaniline (0.46 g) and 2-chlorobenzimidazole (0.5 g) were mixed in a flask and then kept at 170° C. for 30 min. After cooling, the residue was dissolved out of the flask with 1 N HCl and 10% ethanol at boiling heat. The material dissolved out was then stirred at RT for 30 min, then the insoluble material was filtered off with suction and the filtrate was evaporated. The residue was purified by means of preparative HPLC on RP-18 using acetonitrile/water (0.05% TFA). The clean fractions were combined, the acetonitrile was stripped off, the residue was adjusted to pH 10 with potassium carbonate solution, extracted three times with EA, and then the combined phases were dried, filtered, and concentrated. The residue was taken up using HCl/water and freeze-dried. 227 mg of the title compound were obtained.

LCMS-$R_t$: 3.71 min; MS (ES+, M+H$^+$): 258.0

Example 5

(2,6-Dichlorophenyl)-(5,6-difluoro-1H-benzimidazol-2-yl)amine hydrochloride

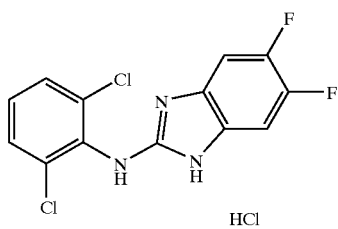

HCl 2,6-Dichlorophenyl isothiocyanate (0.3 g) and 4,5-difluoro-1,2-phenylenediamine (0.21 g) were stirred at RT for 4 h in THF (15 ml) and then concentrated and dried in a high vacuum. The foamy residue was dissolved in ethanol and heated to 70° C. with stirring. Methyl iodide (0.73 ml) was then added dropwise. After three hours, the heating was stopped and the batch was allowed to stand overnight. After concentration, it was taken up using water and EA, and the EA phase was separated off, dried with magnesium sulfate, filtered, and concentrated. The residue was purified by means of preparative HPLC on RP-18 using acetonitrile/water (0.05% TFA). The clean fractions were combined, the acetonitrile was stripped off, the residue was adjusted to pH 10 with potassium carbonate solution, extracted three times with EA, and then the combined phases were dried, filtered, and concentrated. The residue was taken up using 2 N HCl and freeze-dried. 55 mg of the title compound were obtained.

LCMS-$R_t$: 3.83 min; MS (Cl+, M+H$^+$): 314.1

Example 6

(2,6-Dichlorophenyl)-(4-methyl-1H-benzimidazol-2-yl)amine trifluoracetate

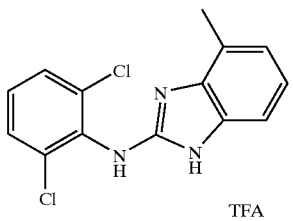

TFA 2,6-Dichlorophenyl isothiocyanate (0.15 g) and 2,3-diaminotoluene (0.09 g) were dissolved in THF (15 ml), the solution was stirred at RT for 4 h and then treated with N,N'-dicyclohexylcarbodiimide (0.23 g), and the mixture was boiled under reflux for 6 h. After allowing to stand overnight, the reaction mixture was concentrated, treated with acetonitrile/water (80:20), the undissolved material was filtered off, and the solution was purified by means of preparative HPLC on RP-18 using acetonitrile/water (0.05% TFA). The product-containing fractions were combined and brought to dryness. Crystallization from EA/ether/heptane yielded 85 mg of the title compound.

LCMS-$R_T$: 3.81 min; MS (ES+, M+H$^+$): 292.0

Example 7

(1H-Benzimidazol-2-yl)-(2-chloro-6-fluorophenyl)amine hydrochloride

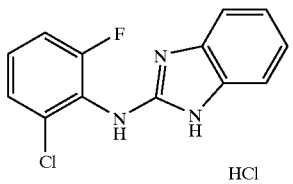

HCl

2-Chloro-6-fluoroaniline (0.48 g) and 2-chlorobenzimidazole (0.5 g) were mixed in a flask and then kept at 170° C. for 30 min. After cooling, the residue was dissolved out of the flask at boiling heat using 1 N HCl and 10% ethanol. The material dissolved out was then stirred at RT for 30 min, then the insoluble material was filtered off with suction and the filtrate was evaporated. The residue was purified by means of preparative HPLC on RP-18 using acetonitrile/water (0.05% TFA). The clean fractions were combined, the acetonitrile was stripped off, the residue was adjusted to pH 10 with potassium carbonate solution, extracted three times with EA, and then the combined phases were dried, filtered, and concentrated. The residue was taken up using HCl/water and freeze-dried. 27 mg of the title compound were obtained.

LCMS-$R_t$: 3.45 min; MS (ES+, M+H$^+$): 262.0

Example 8

(1H-Benzimidazol-2-yl)-(2,6-dibromophenyl)amine trifluoroacetate

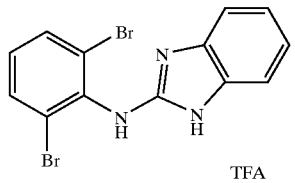

TFA 2,6-Dibromaniline (0.5 g) was dissolved in absolute dioxane (5 ml), trimethylsilyl chloride (0.22 g) was added dropwise through a septum, and the mixture was then stirred at RT for 2 h. 2-Chlorobenzimidazole (0.3 g) dissolved in dioxane was then added and the mixture was boiled under reflux. After 4 h, it was cooled, the dioxane was stripped off, and the residue was heated at 190° C. for 10 min. After cooling, the residue was dissolved out of the flask using 1 N HCl at boiling heat. The insoluble material was then filtered off and the filtrate was evaporated. The residue was purified by means of preparative HPLC on RP-18 using acetonitrile/water (0.05% TFA). The clean fractions were combined and freeze-dried. 2.4 mg of the title compound were obtained.

LCMS-$R_t$: 3.74 min; MS (ES+, M+H$^+$): 369.2

Example 9

2-(2,6-Dichlorophenylamino)-5-fluorobenzimidazole hydrochloride

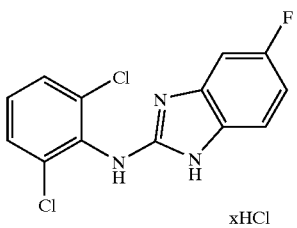

xHCl a) 1-(2-Amino-5-fluorophenyl)-3-(2,6-dichlorophenyl)thiourea

A mixture of 4.37 g (0.0346 mol) of 4-fluoro-1,2-diaminobenzene and 7.07 g (0.0346 mol) of 2,6-dichlorophenyl isothiocyanate in 150 ml of EA was boiled under reflux for 3 hours. After distilling off the solvent, the residue was dissolved in methanol, treated with activated carbon, ⅔ of the solvent volume was distilled off, and the thiourea was allowed to crystallize in an ice bath for a number of hours. 8.9 g of the desired product was obtained. Colorless crystals, 1st m.p.: 175–178° C.; 2nd m.p.: 294–296° C.

MS (ES+, M+H$^+$): 329.9 b) 2-(2,6-Dichlorophenylamino)-5-fluorobenzimidazole Hydrochloride 1-(2-Amino-5-fluorophenyl)-3-(2,6-dichlorophenyl)-thiourea was dissolved in ethanol and treated with 8 equivalents of methyl iodide. The mixture was heated to reflux for 6 h. The solvent was distilled off, the residue was treated with water, then the mixture was rendered weakly alkaline by addition of saturated aqueous sodium hydrogencarbonate solution, and extracted. After distilling off the solvent, the residue was purified by column chromatography on silica gel using a mixture of methylene chloride and methanol (10:1). After distilling off the solvent under reduced pressure, the residue was dissolved using EA, and the solution was treated with excess ethereal hydrochloric acid. The mixture was stirred at RT for approximately 30 minutes, and the crystalline substance was filtered off and recrystallized from a mixture of EA and ethanol. Colorless crystalline product, m.p.: 294–296° C.

MS (Cl+, M+H$^+$): 296

Example 10

2-(2,6-Dichlorophenylamino)-4-fluorobenzimidazole hydrochloride a) 3-Fluoro-2-nitro-phenylhydrazine A mixture of 0.01 M 2,6-difluoronitrobenzene and 0.01 M hydrazine hydrate (99% strength) in 30 ml of THF was stirred overnight at RT (exothermic reaction) and the residue was brought to crystallization after distilling off the solvent by treating with diisopropyl ether. Crystalline substance, m.p.: 93–95° C.

MS (Cl+, M+H$^+$): 172.1 b) 2,3-Diaminofluorobenzene was obtained by hydrogenation of 0.0038 mol of 3-fluoro-2-nitrophenylhydrazine in 50 ml of methanol using palladium on carbon (10% strength) as a catalyst until the absorption of hydrogen ended. After filtration, 2,3-diaminofluorobenzene was obtained as a yellow oily substance.

MS (Cl+, M+H$^+$): 127.2 c) 1-(2-Amino-6-fluorophenyl)-3-(2,6-dichlorophenyl)thiourea was obtained by reaction of 0.011 M 2,3-diaminofluorobenzene with 0.011 M 2,6-dichlorophenyl isothiocyanate in 30 ml of anhydrous THF at RT. After distilling off the solvent, the thiourea was brought to crystallization under EA. Crystalline solid, m.p.: 315° C.

MS (Cl+, M+H$^+$): 330.1 d) 2-(2,6-Dichlorophenylamino)-4-fluorobenzimidazole hydrochloride was obtained analogously to the procedure described in example 9 by reaction of 1-(2-amino-6-fluorophenyl)-3-(2,6-dichlorophenyl)thiourea with 8 equivalents of methyl iodide in ethanol. Colorless crystalline solid having a wide melting point range of 268–296° C. with foaming.

MS (Cl+, M+H$^+$): 296.1

Example 11

2-(2-Trifluoromethyl-6-chlorophenylamino) benzimidazole hydrochloride

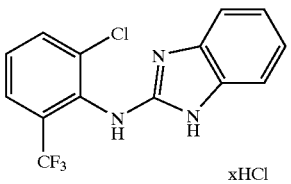

xHCl a) 1-(2-Aminophenyl)-3-(6-chloro-2-trifluoromethylphenyl)urea was obtained by reaction of equivalent amounts of 1,2-diaminobenzene and 2-trifluoromethyl-6-chlorophenyl isocyanate in anhydrous THF, the desired urea derivative crystallizing out after a short time. The mixture was stirred at RT for approximately 20 hours and the crystalline precipitate was filtered off. Decomposition point 310° C.

MS (E+, M+H+): 330.1 b) 2-(2-Trifluoromethyl-6-chlorophenylamino) benzimidazole hydrochloride 0.8 g of 1-(2-aminophenyl)-3-(6-chloro-2-trifluoromethylphenyl)urea was heated under reflux conditions for 5 hours in 10 ml of POCl₃, a clear solution resulting. After distilling off the phosphorus oxychloride under reduced pressure, the oily residue was treated with water, slow crystallization taking place. The crystals were filtered off and chromatographed on silica gel using a mixture of 10 parts of dichloromethane and 1 part of methanol. After distilling off the solvent, the residue was dissolved in EA and rendered strongly acidic using a saturated solution of hydrogen chloride gas in diethyl ether. The crystalline precipitate was filtered off. Colorless to slightly yellowish crystals. M.p.: 255–288° C.

MS (Cl+, M+H+): 312.2

Example 12

2-(2,6-Dichlorophenylamino)-4,5-difluorobenzimidazole hydrochloride a) 1-(2-Amino-5,6-difluorophenyl)-3-(2,6-dichlorophenyl)thiourea was obtained by boiling a mixture of 0.01 M 1,2-diamino-3,4-difluorobenzene with 0.01 M 2,6-dichlorophenyl isothiocyanate in 50 ml of EA for 4 hours. After distilling off the solvent, the thiourea was brought to crystallization under diisopropyl ether. Crystalline solid. M.p.: >310° C.

MS (Cl+, M+H+): 348.0 b) 2-(2,6-Dichlorophenylamino)-4,5-difluorobenzimidazole hydrochloride was obtained analogously to the procedure described in example 9b from 3.2 g of 1-(2-amino-5,6-difluorophenyl)-3-(2,6-dichlorophenyl)thiourea and 10.6 g of methyl iodide. Crystalline solid, m.p.: 228–230° C.

MS (Cl+, M+H+): 314.0

Example 13

2-(2,6-Dichlorophenylamino)-5-hydroxybenzimidazole hydrobromide

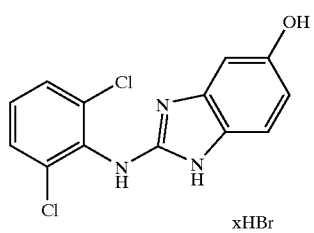

xHBr a) 1-(2-Amino-5-methoxyphenyl)-3-(2,6-dichlorophenyl)thiourea was obtained analogously to the procedure described in example 12a from 0.005 M 1,2-diamino-4-methoxybenzene and 0.005 M 2,6-dichlorophenyl isothiocyanate. Crystalline solid. M.p.: 164–166° C. and fresh crystallization; decomposition point: 200° C.

MS (ES+, M+): 342.0 b) 2-(2,6-Dichlorophenylamino)-5-methoxybenzimidazole hydrochloride was obtained analogously to the procedure described in example 9 by reaction of 0.0025 M 1-(2-amino-5-methoxyphenyl)-3-(2,6-dichlorophenyl)thiourea with 0.0205 M methyl iodide in 20 ml of ethanol. After distilling off the solvent, the residue was dissolved in a little EA, the solution was rendered strongly acidic using a saturated solution of hydrogen chloride gas in diethyl ether, and the crystals were filtered off after a few hours. M.p.: 172–174° C.

MS (Cl+, M+H+): 308.0 c) 2-(2,6-Dichlorophenylamino)-5-hydroxybenzimidazole sydrobromide

A mixture of 0.05 g of 2-(2,6-dichlorophenylamino)-5-methoxybenzimidazole hydrochloride, 0.5 ml of glacial acetic acid, and 0.5 ml of hydrobromic acid (48% strength) was boiled under reflux for 3 hours and the solvent was then distilled off. The solid residue was brought to crystallization under a little EA. 0.02 g of 2-(2,6-dichlorophenylamino)-5-hydroxybenzimidazole hydrobromide was obtained of melting point 265–269° C.

MS (Cl+, M+H+): 294.1

Example 14

2-(2,6-Dichlorophenylamino)-4,5,6,7-tetrafluorobenzimidazole hydrochloride

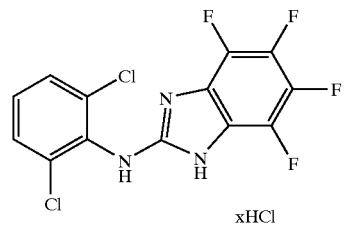

xHCl a) 1-(2-Amino-3,4,5,6-tetrafluorophenyl)-3-(2,6-dichlorophenyl)thiourea was obtained by boiling a mixture of 1 g of 1,2-diamino-3,4,5,6-tetrafluorobenzene with 1.13 g of 2,6-dichlorophenyl isothiocyanate in 30 ml of anhydrous THF for 4 hours.

After distilling off the solvent, the thiourea was brought to crystallization under diisopropyl ether and 1.88 g of 1-(2-amino-3,4,5,6-tetrafluorophenyl)-3-(2,6-dichlorophenyl) thiourea were obtained as a crystalline solid. M.p.: >300° C.

MS (ES+, M+H+): 384.06 b) 2-(2,6-Dichlorophenylamino)-4,5,6,7-tetrafluorobenzimidazole hydrochloride was obtained analogously to the procedure described in example 9b from 1.5 g of 1-(2-amino-3,4,5,6-tetrafluorophenyl)-3-(2,6-dichlorophenyl)thiourea and 4.4 g of methyl iodide and subsequent column chromatography on silica gel using a mixture of 10 parts of EA, 5 parts of n-heptane, 5 parts of dichloromethane, 5 parts of methanol, and 1 part of aqueous concentrated ammonia. Crystalline solid, m.p.: 220–222° C.

MS (Cl+, M+H+): 350.2

Example 15

2-(2,6-Dichlorophenylamino)-4,6-difluorobenzimidazole hydrochloride a) 1,2-Diamino-3,5-difluorobenzene was obtained by hydrogenation of 5 g of 2-amino-3,5-difluoronitrobenzene with 0.8 g of palladium catalyst on carbon at RT and normal pressure. After distilling off the solvent, a dark partially crystalline oil was obtained, which was used without further purification for the preparation of stage b.

b) 1-(2-Amino-4,6-difluorophenyl)-3-(2,6-dichlorophenyl)thiourea was obtained by allowing a mixture of 0.01 M 1,2-diamino-3,5-difluorobenzene with 0.01 M 2,6-dichlorophenyl isothiocyanate in 60 ml of anhydrous THF to stand over the weekend at RT. After distilling off the solvent, the thiourea was brought to crystallization under diisopropyl ether. Crystalline solid, m.p.: 310–314° C.

MS (Cl+, M+H+): 348.1 c) 2-(2,6-Dichlorophenylamino)-4,5-difluorobenzimidazole hydrochloride was obtained analogously to the procedure described in example 9b from 2 g of 1-(2-amino-4,6-difluorophenyl)-3-(2,6-dichlorophenyl) thiourea and 6.4 g of methyl iodide. Crystalline solid, m.p.: 232–234° C.

MS (Cl+, M+H+): 314.2

Example 16

(1H-Benzimidazol-2-yl)-(2-chlorophenyl)amine trifluoroacetate

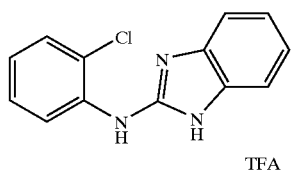

TFA

2-Chloraniline (0.5 g) and 2-chlorobenzimidazole (0.6 g) were mixed in a flask and then kept at 225° C. for 2 h. After cooling, the residue was dissolved out of the flask at boiling heat using 1 N HCl, the insoluble material was filtered off with suction, and the filtrate was adjusted to pH 9–10 using potassium carbonate and concentrated. The residue was treated with hot methanol, the insoluble material was filtered off, the mother liquor was treated with ether, and the precipitate was filtered off again. The mother liquor was concentrated and the residue was crystallized again from methanol/ether. After filtering off the crystals with suction, the mother liquor was concentrated and the residue was purified by means of preparative HPLC on RP-18 using acetonitrile/water (0.05% TFA). The clean fractions were combined and freeze-dried. 100 mg of the title compound were obtained.

LCMS-$R_t$: 3.16 min; MS (Cl+, M+H+): 244.0

Example 17

(1H-Benzimidazol-2-yl)-(2-trifluoromethylphenyl) amine trifluoroacetate

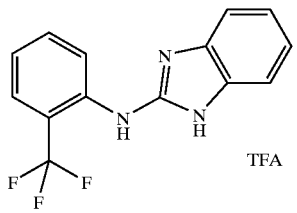

2-Aminobenzotrifluoride (0.5 g) and 2-chlorobenzimidazole (0.47 g) were mixed in a flask and then kept at 225° C. for 2 h. After cooling, the residue was dissolved out of the flask at boiling heat using 1 N HCl and the insoluble matter was filtered off with suction after cooling. The filtrate was concentrated and the residue was purified by means of preparative HPLC on RP-18 using acetonitrile/water (0.05% TFA). The clean fractions were combined and freeze-dried. 52 mg of the title compound were obtained.

LCMS-$R_t$: 3.65 min; MS (Cl+, M+H+): 278.1

Example 18

(1H-Benzimidazol-2-yl)-(2-bromophenyl)amine trifluoroacetate

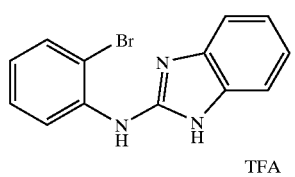

TFA

2-Bromoaniline (0.5 g) and 2-chlorobenzimidazole (0.44 g) were reacted according to example 17. 117 mg of the title compound were obtained.

LCMS-$R_t$: 3.55 min; MS (ES+, M+H+): 288.0

Example 19

(1H-Benzimidazol-2-yl)-o-tolylamine hydrochloride

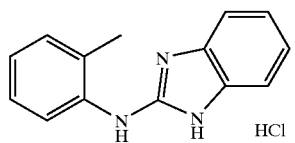

HCl

2-Methylaniline (0.5 g) and 2-chlorobenzimidazole (0.71 g) were mixed in a flask and then kept at 250° C. for 2 h. After cooling, the residue was dissolved out of the flask at boiling heat using 1 N HCl, the insoluble material was filtered off with suction, and the filtrate was evaporated. The residue was purified by means of preparative HPLC on RP-18 using acetonitrile/water (0.05% TFA). The clean fractions were combined, the acetonitrile was stripped off, the residue was rendered alkaline using potassium carbonate solution, extracted three times with EA, and the combined phases were then dried, filtered, and concentrated. The residue was taken up using 2 N HCl and the solution was freeze-dried. 110 mg of the title compound were obtained.

LCMS-$R_t$: 3.54 min; MS (Cl+, M+H+): 224.1

Pharmacological Data:

Test Description:

In this test, the recovery of the intracellular pH ($pH_i$) after an acidification was determined which commences with functional NHE even under bicarbonate-free conditions. For this, the $pH_i$ was determined using the pH-sensitive fluorescent dye BCECF (Calbiochem, the precursor BCECF-AM was employed). The cells were first loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the $pH_i$ by means of calibration curves. The cells were incubated in NH₄Cl buffer (pH 7.4) even in the case of BCECF loading (NH₄Cl buffer: 115 mM NaCl, 20 mM NH₄Cl, 5 mM KCl, 1 mM CaCl₂, 1 mM MgSO₄, 20 mM Hepes, 5 mM glucose, 1 mg/ml of BSA; a pH of 7.4 is set using 1 M NaOH). The intracellular acidification was induced by addition of 975 µl of an NH₄Cl-free buffer (see below) to 25 µl aliquots of the cells incubated in NH₄Cl buffer. The subsequent rate of pH recovery was recorded for two minutes in the case of NHE1, for five minutes in the case of NHE2, and for three minutes in the case of NHE3. For the calculation of the inhibitory potency of the substances tested, the cells were first investigated in buffers in which a complete pH recovery or no pH recovery at all took place. For the complete pH recovery (100%), the cells were incubated in Na+-containing buffer (133.8 mM NaCl, 4.7 mM KCl, 1.25 mM CaCl₂, 1.25 mM MgCl₂, 0.97 mM Na₂HPO₄, 0.23 mM Na₂HPO₄, 5 mM Hepes, 5 mM glucose; a pH of 7.0 is set using 1 M NaOH). For the determination of the 0% value, the cells were incubated in an Na+-free buffer (133.8 mM choline chloride, 4.7 mM KCl, 1.25 mM CaCl₂, 1.25 mM MgCl₂, 0.97 mM K₂HPO₄, 0.23 mM KH₂PO₄, 5 mM Hepes, 5 mM glucose; a pH of 7.0 is set using 1 M NaOH). The substances to be tested were applied in the Na+-containing buffer. The recovery of the intracellular pH at each tested concentration of a substance was expressed in percent of the maximum recovery. The IC value of the respective substance for the individual NHE subtypes was calculated from the percentage values of the pH recovery by means of the program SigmaPlot.

Results:

| Example | IC₅₀ [µM], (rNHE3) |
|---|---|
| 1 | 0.53 |
| 2 | 0.47 |
| 3 | 0.64 |
| 4 | 0.49 |
| 5 | 0.78 |
| 6 | 0.39 |
| 7 | 0.52 |
| 8 | 0.65 |
| 9 | 1.0 |
| 10 | 3.2 |
| 11 | 0.83 |
| 12 | 2.9 |
| 13 | 1.1 |
| 14 | 5.6 |
| 15 | 1.6 |
| 16 | 0.63 |
| 17 | 3.5 |
| 18 | 1.2 |
| 19 | 3.5 |

What is claimed is:

1. A method for treating disorders of the respiratory drive, comprising administering to a patient in need thereof an effective amount of at least one compound of Formula I

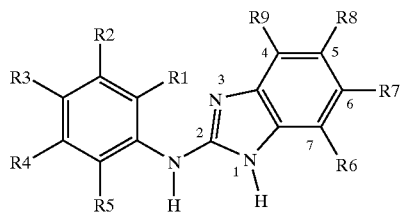

in which:
R1 and R5 are, independently of one another, H, F, Cl, Br, I, CN, alkyl having 1 to 4 carbon atoms, in which alkyl is unsubstituted or partially or completely substituted by fluorine; or
R1 and R5 are cycloalkyl having 3 to 7 carbon atoms, which is unsubstituted or partially or completely substituted by fluorine; or
R1 and R5 are OH or O-alkyl having 1 to 4 carbon atoms, in which alkyl is unsubstituted or partially or completely substituted by fluorine; or
R1 and R5 are OCOR10, NR11R12, COR13, COOH, COOR14, CONR11R12, or —(O)ₙ—SOₘR15, in which n is 0 or 1 and m is 0, 1, or 2; or
R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or ($C_1$–$C_4$)-alkylsulfonyl, in which the alkyl groups are unsubstituted or partially or completely substituted by fluorine;
R16 and R17 are H or alkyl having 1 to 4 carbon atoms, in which alkyl is unsubstituted or partially or completely substituted by fluorine;
R10 is H or alkyl having 1 to 4 carbon atoms, in which alkyl is unsubstituted or partially or completely substituted by fluorine;
R11 and R12 are, independently of one another, H or alkyl having 1 to 4 carbon atoms, in which alkyl is unsubstituted or partially or completely substituted by fluorine, and at least one $CH_2$ group of said alkyl is optionally replaced be by O or NR18; or
R11 and R12, together with the nitrogen atom to which they are bonded, form a 5-, 6-, or 7-membered ring; or
R11 and R12 are COR19 or $SO_2$R20;
R18, R19, and R20 are, independently of one another, H or alkyl having 1 to 4 carbon atoms, in which alkyl is unsubstituted or partially or completely substituted by fluorine;
R13 and R14 are alkyl having 1 to 4 carbon atoms, which is unsubstituted or partially or completely substituted by fluorine;
R15 is alkyl or O-alkyl, in which the alkyl groups have 1 to 4 carbon atoms and are unsubstituted or partially or completely substituted by fluorine; or
R15 is OH or NR21R22;
R21 and R22 are, independently of one another, H or alkyl having 1 to 4 carbon atoms, in which alkyl is unsubstituted or partially or completely substituted by fluorine, and at least one $CH_2$ group of said alkyl is optionally replaced by O— or NR23;
R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

2. The method of claim 1, wherein the disorder of the respiratory drive is sleep-related respiratory disorder.

3. The method of claim 2, wherein the sleep-related respiratory disorder is sleep apnea.

4. The method of claim 2, wherein the sleep-related respiratory disorder is snoring.

5. A method for treating acute and chronic kidney diseases, comprising administering to a patient in need thereof an effective amount of at least one compound of Formula I

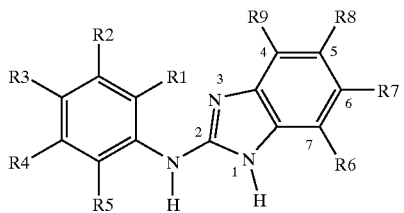

in which:

R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or —$(O)_n$—$SO_mR15$, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or $(C_1–C4)$-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one $CH_2$ group of said alkyl is optionally replaced be by O or NR18; or R11 and R12, together with the nitrogen atom to which they are bonded, form a 5-, 6-, or 7-membered ring; or R11 and R12 are COR19 or $SO_2R20$;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one $CH_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

6. The method of claim 5, wherein the acute and chronic kidney diseases are acute kidney failure and chronic kidney failure.

7. A method for treating disorders of intestinal function, comprising administering to a patient in need thereof an effective amount of at least one compound of Formula I

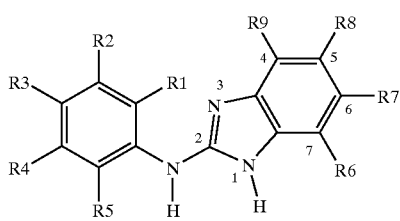

in which:
R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, OCOR14, CONR11R12, or —(O)$_n$—SO$_m$R15, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or ($C_1$–$C_4$)-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one CH$_2$ group of said alkyl is optionally replaced be by O or NR18; or R11 and R12, together with the nitrogen atom to which they are bonded, form a 5-, 6-, or 7-membered ring; or R11 and R12 are COR19 or SO$_2$R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one CH$_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one CH$_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

8. A method for treating disorders of bile function, comprising administering to a patient in need thereof an effective amount of at least one compound of Formula I

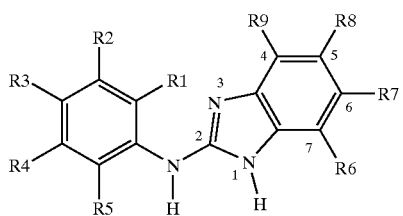

in which:
R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or —(O)$_n$—SO$_m$R15, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or (C₁–C₄)-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one CH₂ group of said alkyl is optionally replaced be by O or NR18; or R11 and R12, together with the nitrogen atom to which they are bonded, form a 5-, 6-, or 7-membered ring; or R11 and R12 are COR19 or SO₂R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one CH₂ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one CH₂ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

9. A method for treating ischemic conditions of peripheral organs and limbs, comprising administering to a patient in need thereof an effective amount of at least one compound of Formula I

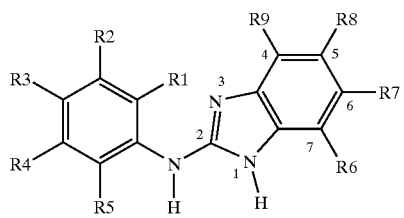

in which:

R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or —(O)ₙ—SOₘR15, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or (C₁–C₄)-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one CH₂ group of said alkyl is optionally replaced be by O or NR18; or R11 and R12, together with the nitrogen atom to which they are bonded, form a 5-, 6-, or 7-membered ring; or R11 and R12 are COR19 or SO₂R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one CH₂ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, aikyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

10. A method for treating a patient during surgical operations, comprising administering to a patient in need thereof an effective amount of at least one compound of Formula I in which:

R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or —(O)$_n$—SO$_m$R15, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or $(C_1–C_4)$-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one $CH_2$ group of said alkyl is optionally replaced be by O or NB18; or R11 and R12, together with the nitrogen atom to which they are bonded, form a 5-, 6-, or 7-membered ring; or R11 and R12 are COR19 or SO$_2$R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one $CH_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

11. A method of claim 10, where said surgical operations is an organ transplantation.

12. A method of claim 10, wherein said patient is a recipient of an organ transplant.

13. A method of claim 10, wherein said patient is a donor of an organ transplant.

14. A method for treating an organ transplant, which comprises contacting an organ transplant with an effective amount of at least one compound of Formula I

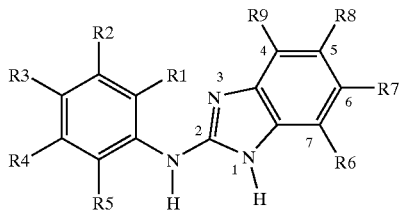

in which:
R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or —(O)$_n$—SO$_m$R15, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or (C$_1$–C$_4$)-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one CH$_2$ group of said alkyl is optionally replaced be by O or NR18; or R11 and R12, together with the nitrogen atom to which they are bonded, form a 5-, 6-, or 7-membered ring; or R11 and R12 are COR19 or SO$_2$R20;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one CH$_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one CH$_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

15. A method of claim 14, wherein said contacting occurs during storage of said organ transplant.

16. A method of claim 14, wherein said contacting occurs during transfer of said organ transplant.

17. A method for treating illnesses in which cell proliferation is a primary or secondary cause, comprising administering to a patient in need thereof an effective amount of at least one compound of Formula I

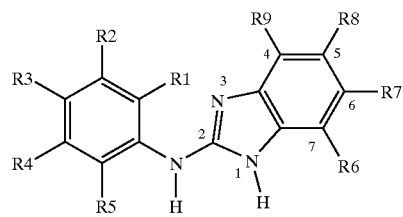

in which:
R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or —(O)$_n$—SO$_m$R15, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or $(C_1-C_4)$-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one $CH_2$ group of said alkyl is optionally replaced be by O or NR18; or R11 and R12, together with the nitrogen atom to which they are bonded, form a 5-, 6-, or 7-membered ring; or R11 and R12 are COR19 or $SO_2R20$;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one $CH_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by flourine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

18. A method for treating attack by ectoparasites in human and veterinary medicine, comprising administering to a patient in need thereof an effective amount of at least one compound of Formula I in which:

R1 and R5 are, independently of one another, H, F, Cl, Br, I, CN, alkyl having 1 to 4 carbon atoms, in which alkyl is unsubstituted or partially or completely substituted by fluorine; or R1 and R5 are cycloalkyl having 3 to 7 carbon atoms, which is unsubstituted or partially or completely substituted by fluorine; or R1 and R5 are OH or O-alkyl having 1 to 4 carbon atoms, in which alkyl is unsubstituted or partially or completely substituted by fluorine; or R1 and R5 are OCOR10, NR11R12, COR13, COOH, COOR14, CONR11R12, or $-(O)_n-SO_mR15$, in which n is 0 or 1 and m is 0, 1, or 2; or R1 and R5 are O-phenyl, in which phenyl is unsubstituted or substituted by one to three substituents selected from F, Cl, Br, I, alkyl having 1 to 4 carbon atoms, OH, O-alkyl having 1 to 4 carbon atoms, NR16R17, CN, or $(C_1-C_4)$-alkylsulfonyl, in which the alkyl groups are unsubstituted or partially or completely substituted by fluorine;

R16 and R17 are H or alkyl having 1 to 4 carbon atoms, in which alkyl is unsubstituted or partially or completely substituted by fluorine;

R10 is H or alkyl having 1 to 4 carbon atoms, in which alkyl is unsubstituted or partially or completely substituted by fluorine;

R11 and R12 are, independently of one another, H or alkyl having 1 to 4 carbon atoms, in which alkyl is unsubstituted or partially or completely substituted by fluorine, and at least one $CH_2$ group of said alkyl is optionally replaced be by O or NR18; or R11 and R12, together with the nitrogen atom to which they are bonded, form a 5-, 6-, or 7-membered ring; or R11 and R12 are COR19 or $SO_2R20$;

R18, R19, and R20 are, independently of one another, H or alkyl having 1 to 4 carbon atoms, in which alkyl is unsubstituted or partially or completely substituted by fluorine;

R13 and R14 are alkyl having 1 to 4 carbon atoms, which is unsubstituted or partially or completely substituted by fluorine;

R15 is alkyl or O-alkyl, in which the alkyl groups have 1 to 4 carbon atoms and are unsubstituted or partially or completely substituted by fluorine; or R15 is OH or NR21R22;

R21 and R22 are, independently of one another, H or alkyl having 1 to 4 carbon atoms, in which alkyl is unsubstituted or partially or completely substituted by fluorine, and at least one $CH_2$ group of said alkyl is optionally replaced by O— or NR23;

R23 is H or alkyl having 1 to 4 carbon atoms, in which alkyl is unsubstituted or partially or completely substituted by fluorine; or R21 and R22, together with the nitrogen atom to which they are bonded, form a 5-, 6-, or 7-membered ring;

R2, R3, and R4 are, independently of one another, H or F;

R6, R7, R8, and R9 are, independently of one another, H, F, Cl, Br, I, CN, alkyl, or O-alkyl, in which the alkyl groups have 1 to 4 carbon atoms and are unsubstituted or partially or completely substituted by fluorine; or R6, R7, R8, and R9 are cycloalkyl having 3 to 7 carbon atoms, which is unsubstituted or partially or completely substituted by fluorine; or R6, R7, R8, and R9 are OH, OCOR24, or NR25R26;

R24 is H or alkyl having 1 to 4 carbon atoms, in which alkyl is unsubstituted or partially or completely substituted by fluorine;

R25 and R26 are, independently of one another, H or alkyl having 1 to 4 carbon atoms, in which alkyl is unsubstituted or partially or completely substituted by fluorine; or R25 and R26 are COR27; or R25 and R26, together with the nitrogen atom to which they are bonded, form a 5-, 6-, or 7-membered ring, and at least one $CH_2$ group thereof is optionally replaced by O or NR18;

R27 is H or alkyl having 1 to 4 carbon atoms, in which alkyl is unsubstituted or partially or completely substituted by fluorine; or a pharmaceutically tolerable salt thereof.

* * * * *

UNITED STATES PATENT AND TRADEMARK OFFICE
CERTIFICATE OF CORRECTION

PATENT NO.     : 6,958,357 B2
DATED          : October 25, 2005
INVENTOR(S)    : Hofmeister et al.

It is certified that error appears in the above-identified patent and that said Letters Patent is hereby corrected as shown below:

<u>Column 24,</u>
Line 44, "replaced be by" should read -- replaced by --.

<u>Column 26,</u>
Line 2, "($C_1$-C4)-alkylsulfonyl," should read -- ($C_1$-$C_4$)-alkylsulfonyl; --.
Line 15, "replaced be by" should read -- replaced by --.

<u>Column 27,</u>
Line 31, "OCOR14," should read -- COOR14, --.
Line 37, "($C_1$-$C_4$)-alkvlsulfonyl," should read -- ($C_1$-$C_4$)-alkylsulfonyl, --.
Line 50, "replaced be by" should read -- replaced by --.

<u>Column 29,</u>
Line 14, "replaced be by" should read -- replaced by --.

<u>Column 30,</u>
Line 44, "replaced be by" should read -- replaced by --.

<u>Column 31,</u>
Line 6, "aikyl," should read -- alkyl --.
Line 60, "CI," should read -- Cl, --.

<u>Column 32,</u>
Line 8, "replaced be by" should read -- replaced by --.
Line 8, "NB18;" should read -- NR18; --.

<u>Column 33,</u>
Line 47, "replaced be by" should read -- replaced by --.

<u>Column 35,</u>
Line 16, "replaced be by" should read -- replaced by --.
Line 20, "R12are COR 19" should read -- R12 are COR19 --.

UNITED STATES PATENT AND TRADEMARK OFFICE
CERTIFICATE OF CORRECTION

PATENT NO.     : 6,958,357 B2
DATED          : October 25, 2005
INVENTOR(S)    : Hofmeister et al.

It is certified that error appears in the above-identified patent and that said Letters Patent is hereby corrected as shown below:

Column 36,
Line 45, "replaced be by" should read -- replaced by --.

Signed and Sealed this

Twenty-eighth Day of March, 2006

JON W. DUDAS
*Director of the United States Patent and Trademark Office*